United States Patent [19]
Butler

[11] Patent Number: 5,253,948
[45] Date of Patent: Oct. 19, 1993

[54] CONNECTOR FOR RELEASABLY CONNECTING AND LOCKING A FIRST MEMBER TO A SECOND MEMBER

[76] Inventor: Peter R. Butler, 504 Riverside Drive, London, Ontario, Canada

[21] Appl. No.: 737,645

[22] Filed: Jul. 30, 1991

Related U.S. Application Data

[63] Continuation-in-part of Ser. No. 223,135, Jul. 22, 1988, abandoned.

[51] Int. Cl.⁵ .................... B25G 3/24; A46B 17/00
[52] U.S. Cl. .................... 403/289; 15/176.6; 403/348; 403/350
[58] Field of Search ............. 15/144 R, 145, 167.1, 15/167.2, 176.1, 176.6; 4/507, 496; 285/7, 276, 282, 396; 403/289, 290, 316, 341, 348, 204, 293, 349, 342, 343, 350

[56] References Cited

U.S. PATENT DOCUMENTS

| | | |
|---|---|---|
| 607,105 | 7/1898 | Wilkinson .................... 15/176.6 |
| 759,490 | 5/1904 | Yates .................... 15/167.1 |
| 935,493 | 9/1909 | Gramm et al. .................... 16/167.1 |
| 1,138,926 | 5/1915 | Bernett .................... 403/349 |
| 1,695,565 | 12/1928 | Thomas .................... 403/290 |
| 2,246,670 | 6/1941 | Earl .................... 403/289 |
| 2,416,684 | 3/1947 | Fischer . | |
| 3,021,160 | 2/1962 | Hooks . | |
| 3,401,371 | 9/1968 | Hammond . | |
| 3,719,378 | 3/1973 | Windsor . | |
| 3,858,910 | 1/1975 | Oetiker .................... 403/349 |
| 3,964,364 | 6/1976 | Poe . | |
| 4,012,155 | 3/1977 | Morris . | |
| 4,141,619 | 2/1979 | DeLuca . | |
| 4,227,276 | 10/1980 | Ginsburg et al. .................... 15/176.1 |
| 4,245,368 | 1/1981 | Cotey et al. .................... 15/229.1 |
| 4,392,279 | 7/1983 | Schwager .................... 403/349 |
| 4,592,109 | 6/1986 | Borea et al. .................... 15/172 |
| 4,642,837 | 2/1987 | Nichols et al. .................... 15/145 |
| 4,654,922 | 4/1987 | Chen .................... 15/176.1 |
| 4,683,604 | 8/1987 | Rueb .................... 15/176.1 |
| 4,797,958 | 1/1989 | Guzzini .................... 4/507 |
| 4,811,445 | 3/1989 | Lagieski et al. .................... 15/167.1 |

FOREIGN PATENT DOCUMENTS

| | | |
|---|---|---|
| 2131641 | 10/1972 | France . |
| 2595221 | 9/1987 | France .................... 15/167.1 |
| 8303829 | 6/1985 | Netherlands .................... 15/176.6 |
| 2134965 | 8/1984 | United Kingdom . |

*Primary Examiner*—Chris K. Moore
*Assistant Examiner*—Charles Cooley
*Attorney, Agent, or Firm*—McFadden, Fincham, Marcus & Anissimoff

[57] ABSTRACT

A connector for releasably connecting and locking a first member to a second member is provided. The connector includes a first member having a connecting element extending from the first member; a second member having a locking element extending from the second member; and an intermediate member having two ends and a passage extending through the intermediate member from one end to the other end. One end of the intermediate member is rotatably attached to the second member so that the locking element of the second member extends into the passage. The other end of the intermediate member is releasably attached to the first member so that the connecting element of the first member extends into the passage. The first member can be locked to the intermediate member by rotating the locking element relative to the connecting element. The connector may be used to releasably connect and lock a toothbrush head to a toothbrush handle.

4 Claims, 7 Drawing Sheets

CONNECTOR FOR RELEASABLY CONNECTING AND LOCKING A FIRST MEMBER TO A SECOND MEMBER

This is a continuation-in-part of application Ser. No. 07/223135, filed Jul. 22, 1988, now abandoned.

FIELD OF THE INVENTION

This invention relates to a connector for releasably connecting and locking a first member to a second member and, in particular, for releasably connecting and locking a toothbrush handle to a toothbrush head.

BACKGROUND OF THE INVENTION

It is desirable to provide a two-part toothbrush comprising a first handle portion and a second head portion. This necessitates a connection between the two portions. One reason for providing a two-part toothbrush is that toothbrushes readily wear out during use. Rather than being thrown out, the toothbrush is usually used beyond its useful life. A further reason for providing a two-part toothbrush is that a one-part toothbrush is ill-adapted for travelling and storage. In addition, it would be advantageous to have a clean toothbrush head available for use at one's destination or at any location at which it is desired to brush one's teeth. To make the toothbrush a more versatile item of dental hygiene, it would also be advantageous to provide different types of heads for use with a single handle.

There are may types of connectors in the prior art but there still exists a need for a useful connector for releasably connecting and locking a toothbrush head to a handle. The main disadvantage of prior art connectors, such as the one disclosed in U.S. Pat. No. 2,416,684 to Fischer, is the risk of disconnection of the portions during actual use of the toothbrush. The risk of disconnection may be the result of an improper connection of the two separate portions by the user as well as the substantial forces applied to the toothbrush during use. Consequently, a need exists for a connector which may be positively locked after connection to prevent disconnection during use.

SUMMARY OF THE INVENTION

A connector for releasably connecting and locking a first member to a second member is provided. The connector includes a first member having a connecting element extending axially from one end of the first member; a second member having a locking element extending axially from one end of the second member; and an intermediate member having two ends and a passage extending through the intermediate member from one end to the other end. One end of the intermediate member is rotatably attached to the second member so that the locking element of the second member extends into the passage. The connecting element of the first member extends into the passage at the other end of the intermediate member. The first member may be locked to the intermediate member by the connecting member by rotating the locking element relative to the connecting element.

The intermediate member may be a sleeve having a circular passage extending between the ends of the sleeve. One end of the circular passage may be tapered for receiving the locking element of the second member.

A retaining means may be provided within the passage of the intermediate member for cooperating with and releasably retaining the connecting element. In this way, the locking element may extend into the passage of the intermediate member past the retaining means, such as a shoulder. The connecting element may include two resilient arms. The ends of each resilient arm may have retaining surfaces for cooperation with the shoulder of the intermediate member. Conical guide surfaces at the forward ends of each arm may cooperate with the surface of the passage. The ends of each arm may also have internal cam surfaces for cooperation with the locking element.

A key means may be provided on the connecting element adjacent the first element. A complementary recess adjacent an end of the passage in the intermediate member receives the key means.

The locking element may include a circular rod having a slot extending through the circular rod. Detent means may be provided on the outer surface of the circular rod. In turn, detent grooves having enlarged stop portions may be provided within the passage of the intermediate member for cooperation with the detent means. One end of the circular rod may have a pair of opposed tapered surfaces and a pair of opposed circular conical surfaces for cooperation with the connecting element to thereby lock it within the intermediate member.

The first member may be attached to a toothbrush head or may be one end of a toothbrush head itself. The second member may be attached to a handle for a toothbrush or may be one end of the handle itself.

In accordance with the invention, a method for releasably connecting and locking a first member to a second member is provided. The method includes the steps of:
(a) providing a first member having a connecting element extending from the first member;
(b) providing a second member having a locking element extending form the second member;
(c) providing an intermediate member having two ends and a passage extending through the intermediate member from one end to the other end;
(d) rotatably attaching the intermediate member to the second member so that the locking element of the second member extends into the passage;
(e) releasably attaching the first member to the intermediate member so that the connecting element of the first member extends into the passage;
(f) rotating the locking element relative to the connecting element so that the first member is locked to the intermediate member.

In accordance with the invention, a method for releasably connecting and locking a first member to a second member is provided. The method includes the steps of:
(a) providing a first member having a connecting element extending from the first member;
(b) providing a second member having a locking element extending from the second member and rotatably attached to an intermediate member, the intermediate member having two ends and a passage extending through the intermediate member from one end to the other end so that the locking element of the second member extends into the passage;
(c) releasably attaching the first member to the other end of the intermediate member so that the connecting element of the first member extends into the passage; and (d) locking the first member to the intermediate member by rotating the locking element relative to the connecting element.

BRIEF DESCRIPTION OF THE FIGURES OF THE DRAWINGS

Certain embodiments of the invention are described by way of example, reference being made to the accompanying drawings wherein.

DETAILED DESCRIPTION OF THE PREFERRED EMBODIMENT

Figures 1, 2, 3:
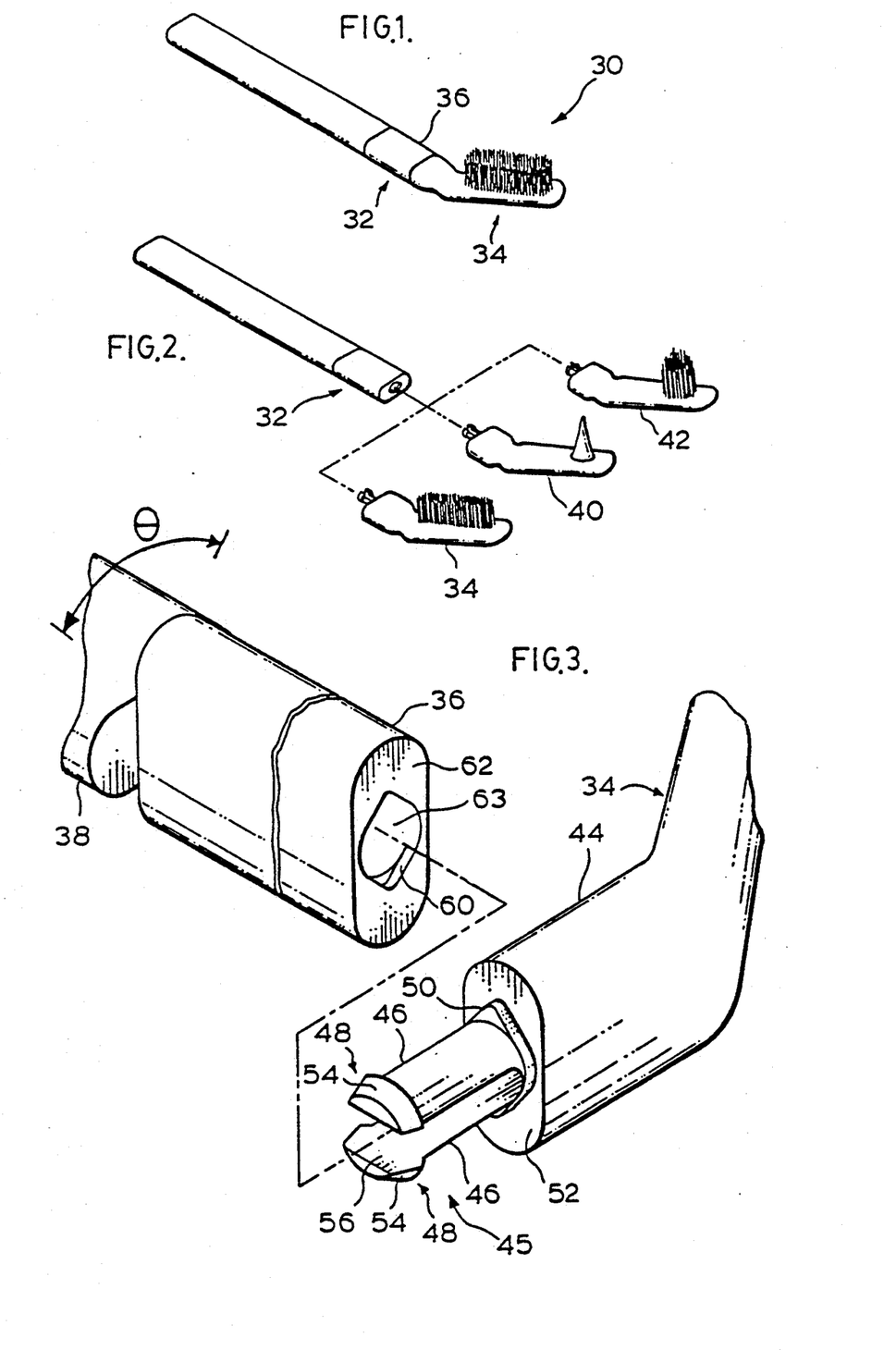
FIG. 1 generally depicts a connected two-part toothbrush.
FIG. 2 is a general view and shows a disconnected two-part toothbrush having two additional connectable heads.
FIG. 3 is a general view of the connector elements and, in particular showing the connecting element.

Referring to FIG. 1, a toothbrush 30 comprises a handle assembly 32 and toothbrush head 34. The handle assembly 32 includes an intermediate portion 36.

Referring to FIG. 2, a typical toothbrush head 34 is shown along with optional toothbrush heads 40 and 42 which may be selectively connected to the handle assembly 32.

Figure 10:
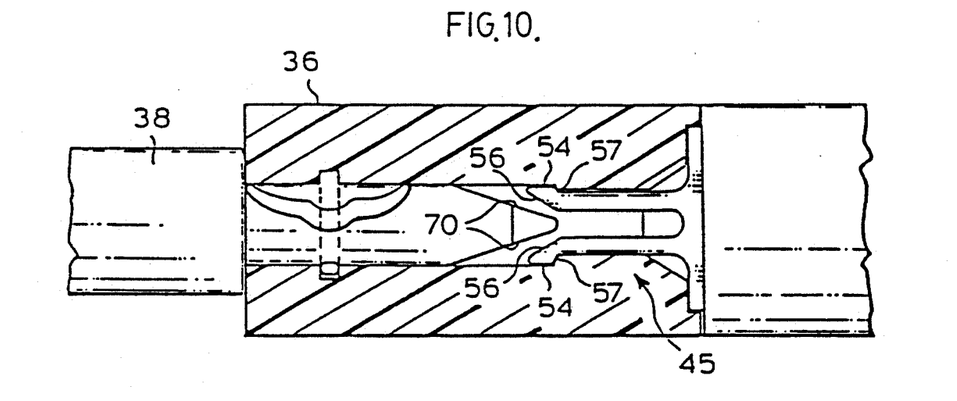
FIG. 10 is a view similar to FIGS. 8 and 9 showing the connecting element releasably connected within the intermediate member.

FIG. 3 shows the assembly point for connecting the toothbrush head 34 to the handle 38. The toothbrush head 34 has an end portion 44 which is ovoid in cross-section. A connecting element 45 comprises a pair of resilient arms 46 which extend axially from the end 52 of the end portion 44 for insertion into a first end of the intermediate member 26 and for connection to the intermediate member 36. The ends 48 of the resilient arms 46 are embossed with forward conical guide surfaces 54 and internal cam surfaces 56. Further, retaining surfaces 57 (as shown in FIG. 10) are provided rearward of the forward conical guide surfaces 54. In the preferred embodiment, there is a key segment 50 surrounding the base of the connecting element 45.

It is to be noted that while the cross section of the parts of the connector is ovoid, a cross section of any other shape may be used.

In FIG. 3, the handle 38 is shown rotated 90° out of registry with intermediate member 36, the condition under which component assembly takes place.

Figure 4:
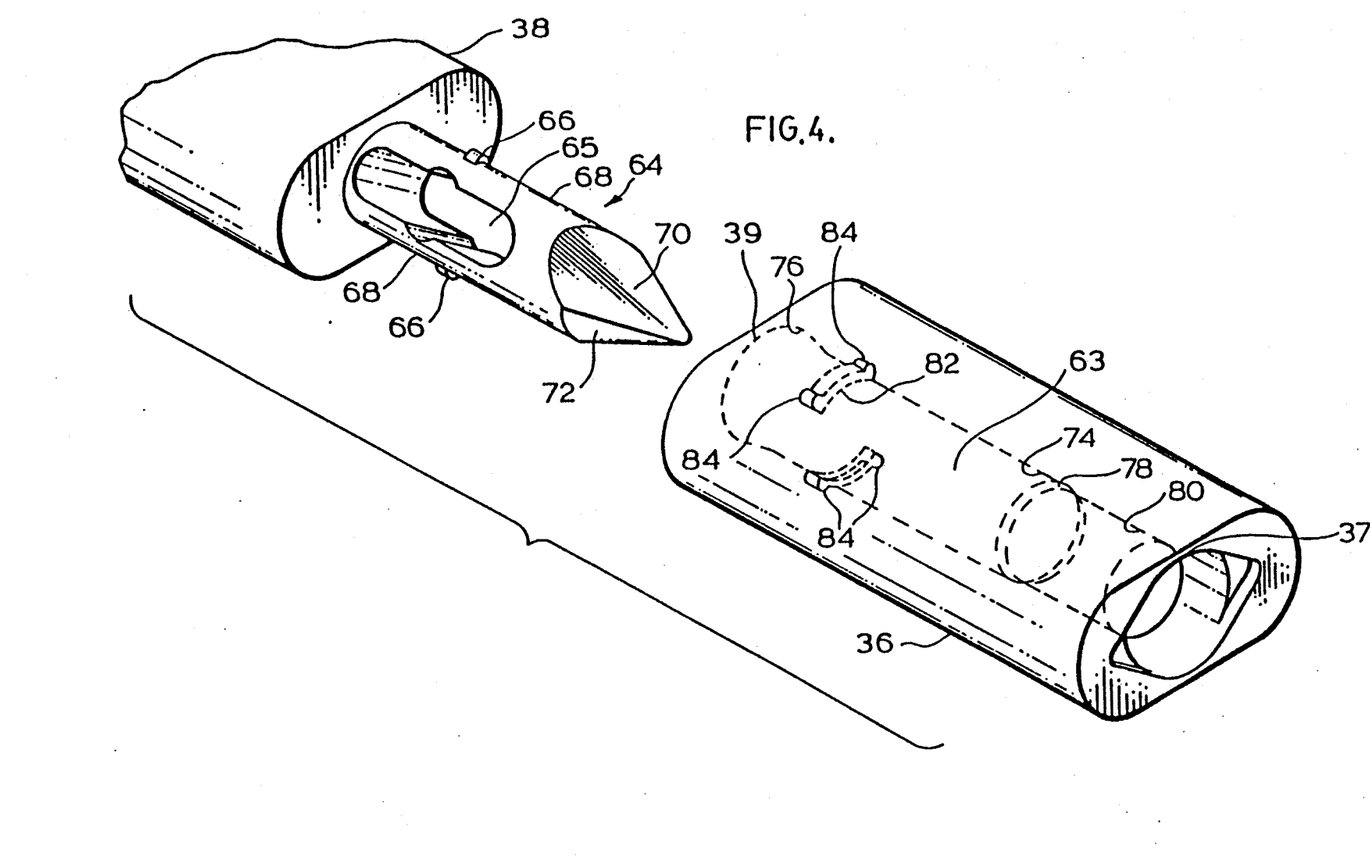
FIG. 4 is a general view of the intermediate member and locking element prior to assembly.

The intermediate member 36, shown in phantom in FIG. 4, is sleeve-like and has two ends, first end 37 and second end 39, respectively. A circular axial passage 63 extends between ends 37 and 39 of the intermediate member 36. A tapered entry 76 is provided at second end 39 of the intermediate member 36. Further, the passage 63 has a first diameter at a first portion 80 extending from said first end and a second larger diameter at a second portion 74 extending from said second end. The difference between the diameters is due to a sloping retaining shoulder 78 within the passage 63 between the first portion 80 and the second portion 74 of the intermediate member 36. Opposing internal detent grooves 82 are provided near second end 39 of the intermediate member 36. Stops 84 at either end of the detent grooves 82 are provided.

The intermediate member 36 is rotatably attached to the handle 38 as will be more particularly described hereinafter. In FIG. 4, handle 38 and sleeve 36 are shown axially aligned and disengaged. The handle 38 has a circular locking element 74 extending axially from one end of the handle 38 for insertion into the second end of the intermediate member 36 as will be more particularly described hereinafter. A central slot 65 is provided in a portion of the locking element 64 which divides the locking element into thin segment portions 68 on the surface of which are located raised detents 66. The diameter of the locking element 64 taken across the raised detents 66 is greater than the diameter of the second portion 74 of the locking element 64. The forward end of the locking element 64 has a pair of opposed tapered surfaces 70 and a pair of opposed conical surfaces 72.

Figure 5:
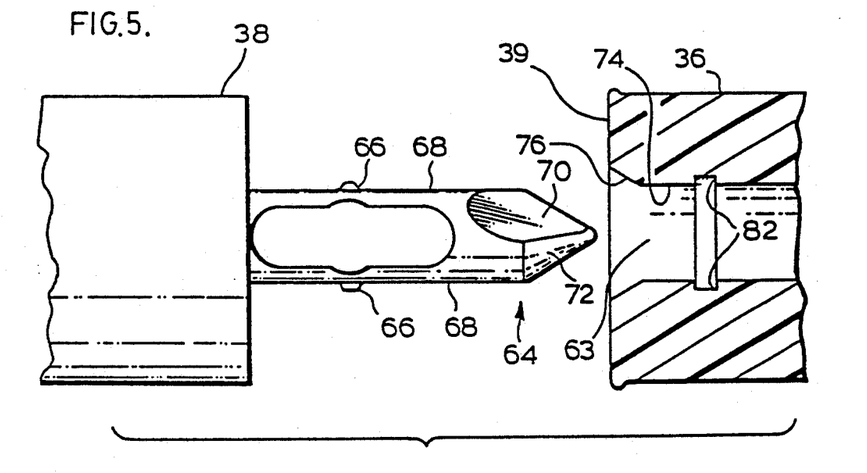
FIG. 5 is a side elevation view of the intermediate member (in cross-section) and locking element prior to assembly.
Figure 6:
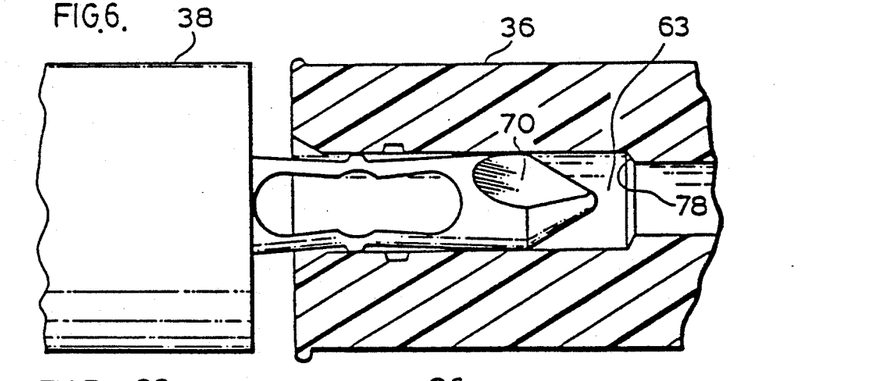
FIG. 6 is a similar view to FIG. 5, with the intermediate member and locking element partially assembled.
Figure 7:
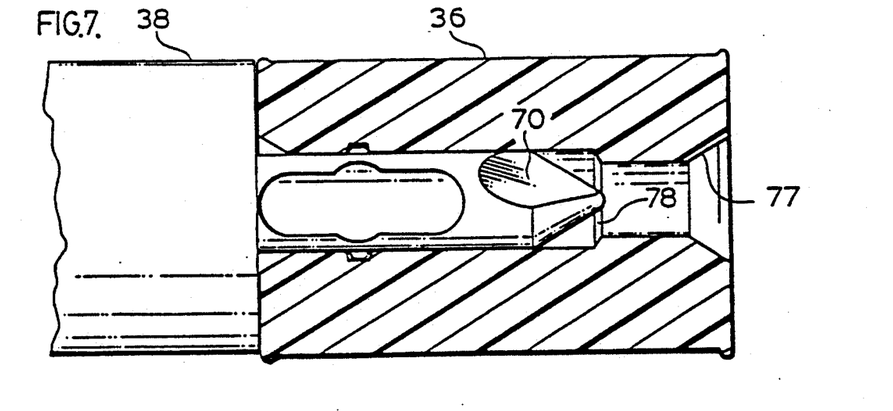
FIG. 7 is a similar view to FIGS. 5 and 6 with the intermediate member and locking element fully assembled.
Figures 15, 16, 17:
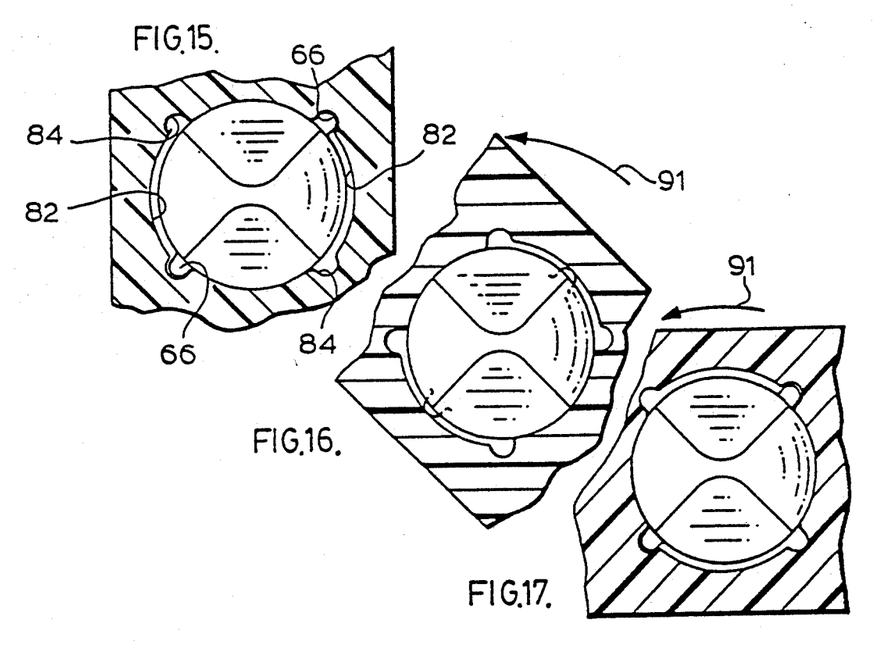
FIG. 15 is an end view, partially in section, showing the rotatable attachment of the intermediate member to the locking element.
FIG. 16 is a view similar to FIG. 16 showing the arrangement of FIG. 15 in relative rotation.
FIG. 17 is a view similar to FIGS. 15 and 16 showing the locking element once rotation is completed.

Referring to FIGS. 5, 6 and 7, the method of assembly of the locking element 64 within the intermediate member 36 is shown. FIG. 5 depicts the components prior to assembly. FIG. 6 depicts initial assembly with the locking element 64 partially inserted into the axial passage 63 of the intermediate member 36. The conical tapered entry 76 of the intermediate member 36 facilitates insertion of the locking element 64. The thin segment portions 68 bias inwardly to permit the passage of the locking member 64 into the passage 63 of the intermediate member 36. The biasing force is released when the detent grooves 82 receive the detents 66 thereby rotatably connecting the handle 38 to the intermediate member 36 along the arc length of the grooves 82. It is to be noted that the segment portions 68 are fully released only at the stops 84 (see FIG. 15). Through all of the intermediate points along the arc length of grooves 82, the segment portions 68 are slightly biased inwardly. The detents 66 snap outwardly into place at the stops 84 and eliminate slack in the rotatable connection. The rotational alignment of the second member to the intermediate member may be maintained during use and the user has a further positive indication when the limit of relative rotation has been reached.

In FIG. 7, it can be seen that the end of the locking element 64 extends to the retaining shoulder 78 of the intermediate member 36.

In the preferred embodiment, the intermediate member 36 is permanently assembled to the handle 38 and all that remains to be done is for the user to connect and lock the toothbrush head 40, 42 or 34 to the handle assembly 32.

Figure 8:
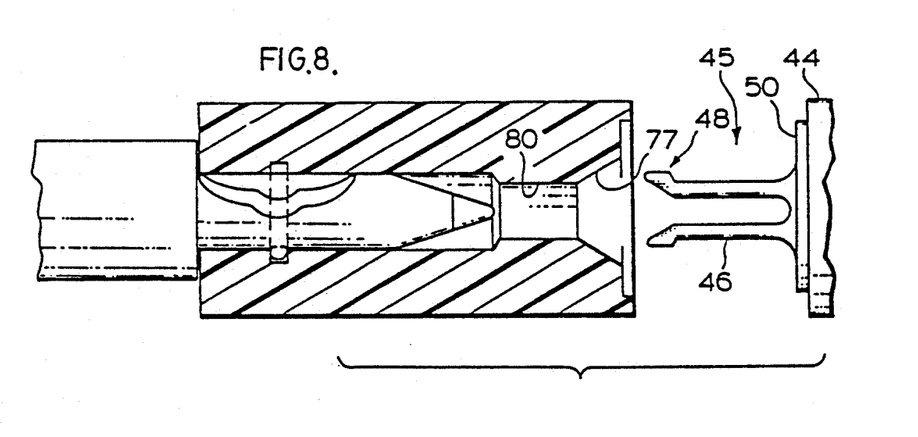
FIG. 8 is a cross-sectional view of the locking element assembled within the intermediate member prior to connection of the connecting element.
Figure 9:
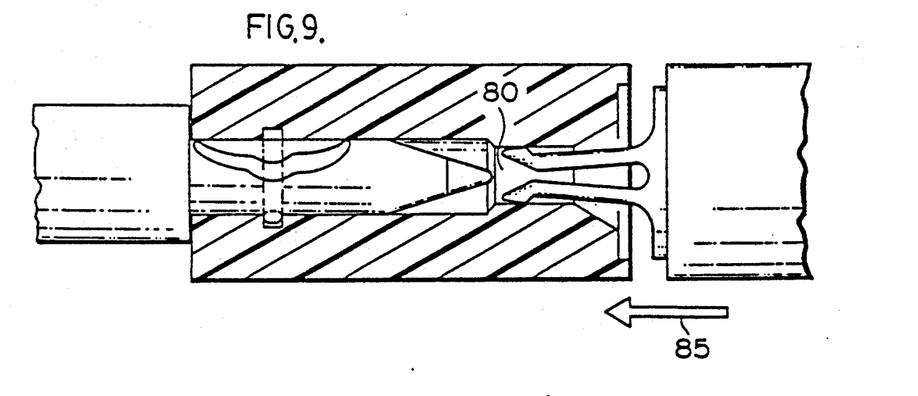
FIG. 9 is a view similar to FIG. 8 showing the connecting element partially inserted into the intermediate member.

Referring to FIGS. 8, 9 and 10, the assembly of the connector is now described. The connecting element 45 is releasably secured within the intermediate member 36 by insertion at the first end 37, into the passage 63. The front portion of the passage 63 contains a recess 60 shaped to receive the key segment 50 of connecting element 45 which aligns the connecting element within the intermediate member and the locking element as will be described. Locking of the connector is achieved by rotating the handle 38 through angle 0 (shown in FIG. 3) relative to the connecting element 45.

Figure 12:
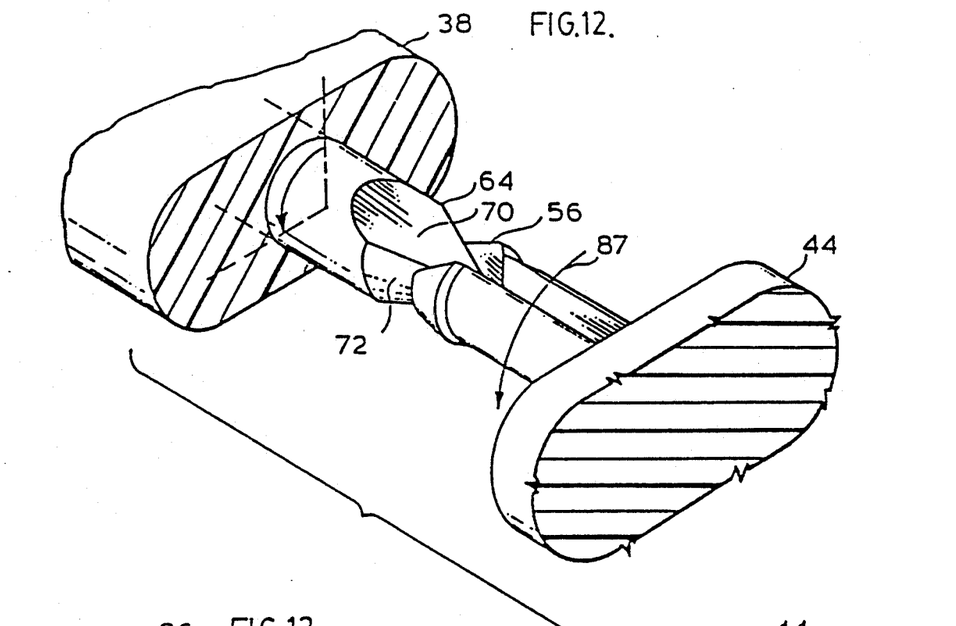
FIG. 12 is a view similar to FIG. 12 showing the locking element rotated relative to the connecting element thereby locking the connection.
Figures 13, 14:
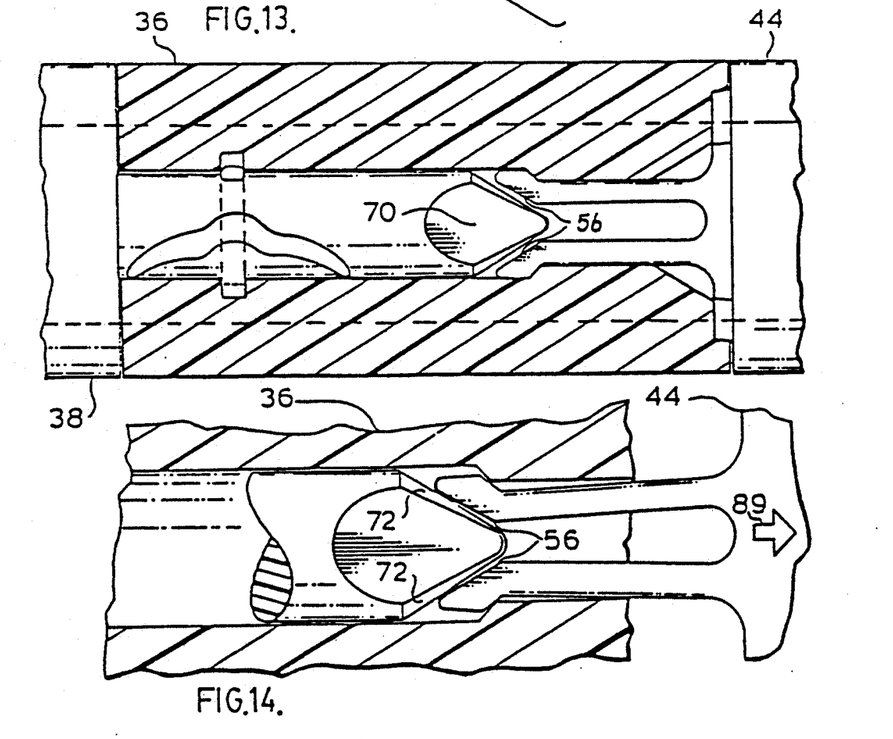
FIG. 13 is a cross-sectional view of the locked connection.
FIG. 14 is an enlarged view of a portion of FIG. 13 showing the effect of tension applied to the connection.

FIG. 9 shows the partially assembled connector. Since the diameter of the first portion 80 of the axial passage 63 is smaller than the diameter presented by the conical guide surfaces 54, the resilient arms 46 bias inwardly during insertion as shown in FIG. 9 and snap outwardly when the retaining shoulder 78 is reached as shown in FIG. 10. At this point, the retaining surfaces 57 of the arms 46 engage the shoulder 78 and the key segment 50 is in the recess 60. It is to be noted, however, that at this stage a pulling action on the head 42 will also release of the connecting element 45 from the intermediate member 36. Thus, means must be provided to lock and secure the connecting element 45 within the intermediate member 36. This is generally achieved by rotation of the handle 38 and consequent rotation of the locking element 64 such that the conical surfaces 72 of the locking element 64 are rotated to cooperate with cam surfaces 56 of the connecting element 45 as shown in FIGS. 12 and 13. This prevents the arms 46 from being urged inwards and thus permitting withdrawal of the connecting element 45.

Figure 11:
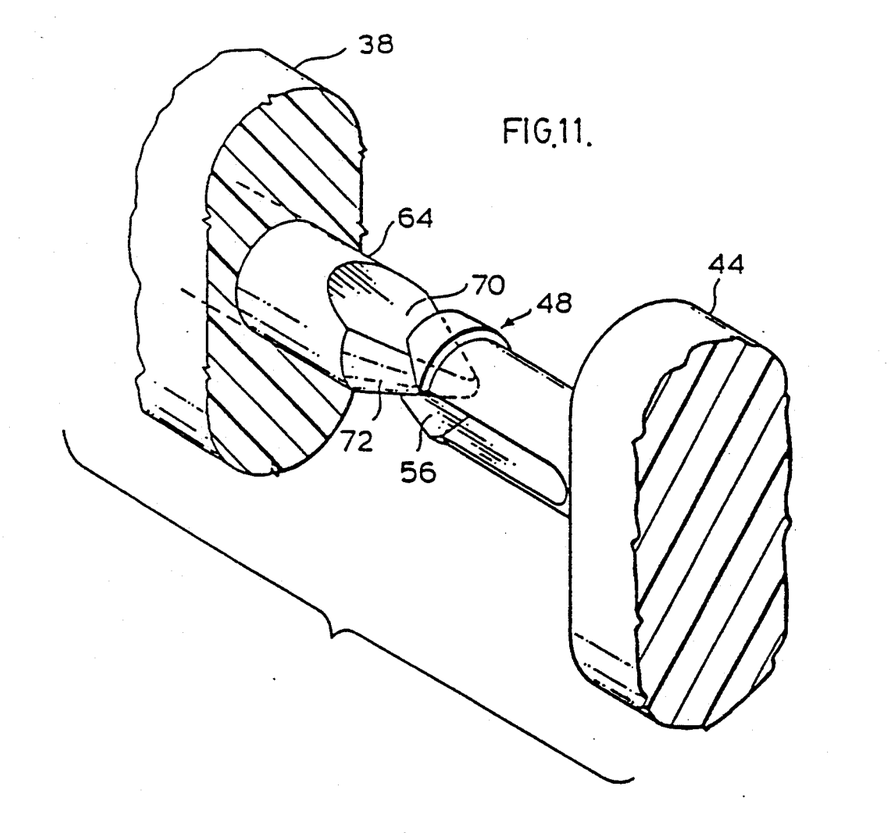
FIG. 11 is a general view of the FIG. 10 assembly, having a portion of the intermediate member removed.

It can be appreciated that the ovoid cross-section of the connector will give a visual indication of relative rotation between the handle 38 and intermediate member 36. Thus, in FIG. 3 the handle 38 is shown at one limit of its relative rotation which corresponds to the locking element 64 being aligned within the intermediate member 36 to present the tapered surfaces 70 to the cam surfaces 56. The connecting element 45 is releasably secured within the intermediate member 36 in this position. The tapered surfaces present a narrow wedge to the cam surfaces 72 and the connecting element 45 may be both inserted and withdrawn. Rotation of the handle 38 to the other limit of rotation, as shown in FIGS. 11 and 12, results in a toothbrush having a smooth external surface and locks the connector by presenting the conical surfaces 72 to the cam surfaces 56 on the connecting element. The conical surfaces 72 present a thick cone to the cam surfaces 56 which locks the connecting element 49 within the intermediate member 36 behind the retaining shoulder 78. In the locked condition a pivoting action on the first member will result in the cam surfaces 56 immediately abutting against the conical surfaces 72 which prevents the resilient arms 46 from biasing inwardly and they remain secured behind the retaining shoulder 78.

It should also be noted that the connector may be reversed so that the locking element may be located on the first member and the connecting element on the second member.

While preferred embodiments of the invention have been described in detail, it will be understood by those skilled in the art that variations may be made to such embodiments without departing from the spirit of the invention or the scope of the appended claims.

I claim:

1. A connector for releasably connecting a first member to a second member, comprising:

a first member having an integral connecting member extending axially from one end, said connecting member including opposed deflecting arms having free ends and a retaining surface on the free end of each arm;

a second member having an integral locking member extending axially from a forward end, said locking member including outwardly and rearwardly inclined surfaces at a forward end, said outwardly and rearwardly inclined surfaces comprising a pair of opposed flat tapered surfaces and an opposed pair of conical surfaces;

said one end of said first member and said forward end of said second member spaced axially apart and in opposition;

an intermediate member having two ends and a passageway extending through the intermediate member from a first end to a second end, and an engagement surface in said passageway facing towards said first end, for cooperation with said retaining surfaces on said arms of said first member;

said locking member adapted to be inserted into said passageway through said second end, and said connecting member adapted to be inserted into said passageway through said first end, said locking member and said connecting member being axially aligned; said opposed conical surfaces outwardly biasing said arms to engage said retaining surfaces on said connecting member with said engagement surface in said passageway, said opposed flat tapered surfaces permitting said arms to deflect inwards on rotation of said locking member in said intermediate member, to permit removal of said connecting member from said passageway;

means for reciprocally engaging said intermediate member with said second member comprising at least one groove extending in a circumferential direction in said passageway and at least one deflectable detent on said locking member, said detent positioned in said groove on insertion of said locking member in said passageway, for relative reciprocal rotational movement between said intermediate member and said second member.

2. A connector for releasably connecting and locking a first member to a second member in alignment on a longitudinal axis, comprising:

a first member having an integral connecting member extending from an end of said first member, said connecting member having two resilient arms, the ends of each arm having a retaining surface;

a second member having an integral locking member extending from an end of said second member, said locking member including an end surface for cooperation with said ends of said arms on said connecting member;

an intermediate member having two ends and a passage extending through the intermediate member from one end to the other, a shoulder within said passage, said shoulder cooperating with said retaining surfaces on said arms for releasably retaining said connecting member in said passage, and releasable connecting means adjacent said one end for releasably connecting said intermediate member to said second member, said releasable connecting means comprising outwardly extending projections on said locking member, said projections resiliently displaceable inwardly toward said longitudinal axis and outwardly extending recesses in said passage in said intermediate member, said projections engaging in said recesses when said locking member is pushed into said passage;

wherein the locking member of the second member extends into said passage through said one end and said connecting member extends into said passage through said other end, and said first member can be locked to said intermediate member by relative rotation of the locking member and the connecting member.

3. A connector as set forth in claim 2, wherein the ends of each arm have forward conical guide surfaces for cooperation with the inner surface of the passage.

4. A connector as set forth in claim 2, wherein the ends of each arm have internal cam surfaces for cooperation with the locking member.

* * * * *